United States Patent [19]

Hershenson et al.

[11] Patent Number: 4,961,969
[45] Date of Patent: Oct. 9, 1990

[54] PROCESS FOR RECOVERING MICROBIALLY PRODUCED INTERFERON-$\beta$

[75] Inventors: Susan Hershenson, San Francisco; Ze'ev Shaked, Berkeley; Jody Thomson, Albany, all of Calif.

[73] Assignee: Cetus Corporation, Emeryville, Calif.

[21] Appl. No.: 48,686

[22] Filed: May 11, 1987

[51] Int. Cl.$^5$ .................... C12P 21/00; A61K 45/02; C07K 15/26
[52] U.S. Cl. .................... 435/69.51; 424/85.6; 530/351
[58] Field of Search .................... 435/68, 172.3, 69.51; 530/351; 424/85.6

[56] References Cited

U.S. PATENT DOCUMENTS

| | | | |
|---|---|---|---|
| 4,462,940 | 7/1984 | Hanisch et al. | 260/112 |
| 4,511,502 | 4/1985 | Builder et al. | 260/112 |
| 4,511,503 | 4/1985 | Olson et al. | 260/112 |
| 4,512,922 | 4/1985 | Jones et al. | 260/112 |
| 4,518,526 | 5/1985 | Olson | 260/112 |
| 4,526,782 | 7/1985 | Uemura et al. | 424/85 |
| 4,530,787 | 7/1985 | Shaked et al. | 424/85.6 |
| 4,530,901 | 7/1985 | Weissmann | 435/70 |
| 4,534,906 | 8/1985 | Johnston | 260/112 |
| 4,541,952 | 9/1985 | Hosoi et al. | 260/112 |
| 4,548,900 | 10/1985 | Nobuhara et al. | 435/68 |
| 4,551,271 | 11/1985 | Hochuli | 260/112 |
| 4,572,798 | 2/1986 | Koths et al. | 424/85.6 |
| 4,599,197 | 7/1986 | Wetzel | 530/405 |
| 4,620,948 | 11/1986 | Builder et al. | 530/419 |

FOREIGN PATENT DOCUMENTS

| | | |
|---|---|---|
| 0028033A2 | 5/1981 | European Pat. Off. . |
| 10145390A2 | 6/1985 | European Pat. Off. . |
| 0150066 | 7/1985 | European Pat. Off. . |
| 0206828 | 12/1986 | European Pat. Off. . |
| 0212960 | 3/1987 | European Pat. Off. . |
| 0225156 | 6/1987 | European Pat. Off. . |
| 0270799 | 6/1988 | European Pat. Off. . |
| 2063882A | 6/1981 | United Kingdom . |
| 0068691 | 1/1983 | United Kingdom . |
| 8505637 | 12/1985 | United Kingdom . |

OTHER PUBLICATIONS

Prouty, W. F. et al., (1975) *J. Biol. Chem.* 250:1112–1122, "Degradation of Abnormal Proteins in *Escherichia coli*".

Klier it al. (1982) "Cloning and Expression of the Crystal Protein Genes from *Bacillus Thuringiensis* Strain Berliner 1715", EMBO Journal 1(7):791–799.

Schnepf et al., (1981) "Cloning and Expression of the *Bacillus Thuringiensis* Crystal Protein Gene in *Escherichia coli*", Proc. Natl. Acad. Sci. USA 78(5).

Williams et al., (1982) "Cytoplasmic Inclusion Bodies in *E. coli* Producing Biosythetic Human Insulin Proteins", *Science* 215:687–689.

Baldwin (1975) "Intermediates in Protein Folding Reactions and the Mechanism of Protein Folding", *Ann. Rev. Biochem.* pp. 453–475.

Kleid et al., Ch. 25 in *Developments in Industrial Microbiol.* 25:317–325 Society for Industrial Microbiol. Arlington, VA, 1984.

Becker et al., "Downstream Processing of Proteins", *Biotech Advs.* (1983) 1:257–261.

Moschera et al. (1986) "Purification of Recombinant Human Fibroblast Interferon Produced in *E. coli*", *Methods Enzymol.* 119:177–183.

Lin et al. (1986) "Purification of Recombinant Human Interferon & Expressed in *E. coli*", *Methods Enzymol.* 119:183.

Arakawa et al. (1985) *J. Biol. Chem.* 260:14435–14439 "Preparation and Characterization of Recombinant DNA-Derived Human Interferon".

*Primary Examiner*—Blondel Hazel
*Attorney, Agent, or Firm*—Albert P. Halluin; Lisabeth E. Murphy

[57] ABSTRACT

An approved procedure for the purification and renaturation of biologically active, bacterially produced IFN-$\beta$ is described. The partially purified material obtained by solubilization of isolated refractile bodies from the recombinant cells is treated to obtain reduction of the protein in the presence of a chaotropic environment and then oxidized after removal of the reducing agent. However, the chaotropic environment is retained during the oxidation. Upon removal of the chaotropic environment, a solubilizing additive is supplied to maintain the IFN-$\beta$ in solution. Further purification by conventional means may also be effected.

21 Claims, No Drawings

PROCESS FOR RECOVERING MICROBIALLY PRODUCED INTERFERON-β

TECHNICAL FIELD

This invention is in the field of biochemical engineering. More particularly, the invention concerns an improved biochemical separation or recovery process in which recombinant interferon-β (rIFN-β) is recovered in substantially pure form from the transformed microorganisms in which it is made, and then oxidized and renatured.

BACKGROUND

Naturally occurring interferons (IFNs) are species-specific proteins, often glycoproteins, produced by various cells upon induction with viruses double-stranded RNAs, other polynucleotides, antigens and mitogens Interferons exhibit multiple biological activities such as antiviral, antiproliferative, immunomodulatory and anticellular functions. At least three distinct types of human interferons have been identified and characterized in terms of their antiviral, antigrowth and activation of natural killer cell (NK) activities. They are produced by leukocytes, lymphocytes, fibroblasts and the immune system and are classified as α, β and γ interferons. These are reported to be different proteins coded for by distinct structural genes.

Native human β-interferon (HuIFN-β) is generally produced by superinducing human fibroblast cultures with Poly-IC (Polyriboinosinic acid and polyribocytidylic acid) and isolating and purifying the HuIFN-β thus produced by chromatographic and electrophoretic techniques. Proteins or polypeptides which exhibit native β-interferon-like properties may also be produced using recombinant DNA technology by extracting poly-A-rich 12S messenger RNA from virally induced human cells, synthesizing double-stranded cDNA using the mRNA as a template, introducing the cDNA into an appropriate cloning vector, transforming suitable microorganisms with the vector, harvesting the bacteria and extracting the HIFN-β therefrom. Nagola, S., et al., *Nature* (1980) 287:411; Yelverton. E., et al., *Nuc Acid Res* (1981) 9:731; Steuli. M., et al., *Proc Natl Acad Sci* (U.S.A.) (1981) 78:2848: European Patent Applications Nos. 2803, published May 6, 1981: 321134, published July 15, 1981; 34307 published August 26, 1981; and Belgian Patent No. 837397, issued July 1, 1981, describe various currently used methods for the production of β-interferon employing recombinant DNA techniques. The expressed proteins of polypeptides have been purified and tested and have been found to exhibit properties similar to those of native IFNs. Bacterially produced IFNs thus appear to have potential therapeutic use as antiviral and antitumor agents and the production of IFNs by such bacterial fermentations is expected to yield sufficiently large quantities of IFN at a relatively low cost of clinical testing.

Further HuIFN-β genes have been altered by, for example, oligonucleotide-directed mutagenesis to produce IFN-β protein analogs thereof, such as the human recombinant cysteine-depleted or cysteine-replaced interferon-β analogs (muteins) disclosed in U.S. Pat. No. 4,588,585, issued May 13, 1986 to Mark et al. Specifically disclosed in that patent is the recombinant IFN-β wherein the cysteine at position 17 is replaced by the neutral amino acid serine. That IFN-β analog is IFN-$β_{ser17}$.

Microbially produced rIFN-β to which this invention applies is not glycosylated and is produced in a denatured state. It is insoluble and, when expressed at high levels, it precipitates intracellularly in the form of "refractile" or "inclusion" bodies which appear as bright spots visible within the enclosure of the cell under a phase contrast microscope at magnifications down to 1000 fold.

The heretofore available methods for recovering microbially produced rIFN-β from the organisms that produce it are described below.

Procedures for recovering and purifying bacterially produced IFNs are described in U.S. Pat. Nos. 4,450,103; 4,315,852; 4,343,735: and 4,343,736; and in Derynch et al., *Nature* (1980) 287:193–197, and Scandella and Kornberg, *Biochemistry* (1971) 10:4447. With these methods the IFN generally is not produced in a sufficiently pure form and in sufficiently large quantities for clinical and therapeutic purposes, and the resulting IFN preparations produced by recombinant DNA techniques have residual amounts of chemicals, such as sodium dodecyl sulfate (SDS) and other surfactants or precipitants used in the extraction and purification steps.

U.S. Pat. No. 4,620,928 describes a process for recovering rIFN-β from an rIFN-β-producing microorganism in which the cell is disrupted; non-rIFN-β proteins are extracted selectively from the disruptate using an aqueous solution of a chaotropic agent such as urea or guanidine; the rIFN-β is solubilized in a denaturing environment, such as guanidine, containing a reducing agent; the reducing agent, after a suitable time, is removed from the solution; the rIFN-β is subjected to a controlled oxidation; and the oxidized rIFN-β is renatured, optionally followed by a combination of HPLC and gel filtration steps.

Commonly owned U.S. Pat. Nos. 4,530,787 and 4,572,978 describe techniques for carrying out the controlled oxidation step referred to above. The former patent uses o-iodosobenzoic acid as an oxidizing agent and the latter uses $Cu^{+2}$ cation as an oxidation promoter.

Copending, commonly owned U.S. applications Ser. Nos. 749,951, filed June 26, 1985 and 843,997, filed Mar. 25, 1986 and entitled "Process for Recovering Refractile Bodies Containing Heterologous Proteins from Microbial Hosts" disclose methods for recovering and purifying refractile bodies of various proteins from *E. coli*. To isolate the refractile material, the processes initially involve disrupting the cell wall and membrane of the host cell, removing greater than 99% by weight of the salts from the disruptate. redisrupting the desalted disruptate, adding a material to the disruptate to create a density or viscosity gradient in the liquid within the disruptate, and separating the refractile material from the cellular debris by high-speed centrifugation. The refractile protein is then solubilized with a solubilizing agent such as SDS, chromatographed to remove high molecular weight contaminants, oxidized, and purified by HPLC, ultrafiltration, and gel filtration. The process of the present invention uses some of the techniques disclosed in these applications to obtain the solubilized IFN-β starting material.

In addition, U.S. Pat. Nos. 4,511,502: 4,511,503; 4,512,922 and 4,518,526: and EPA No. 114,506 describe a similar procedure for recovering heterologous proteins in general from refractile bodies. In such processes, the oxidation and renaturation of the recombinant protein are carried out in a single step.

Copending, commonly owned U.S. application Ser. No. 923,423, filed Oct. 27, 1986 and entitled "Pharmaceutical Compositions of Recombinant Beta-Interferon and Formulation Processes" discloses the use of certain non-ionic detergents for solubilization of recombinant IFN-$\beta$. Many of the detergents and solubilizing agents disclosed therein are useful in the process of the present invention.

Purification procedures for IFN-$\beta$ produced recombinantly in bacteria have been published by Lin, L.S., et al., *Methods in Enzymology* (1986) 119:183; and by Moscheva, J. A., et al., ibid., p. 177.

DISCLOSURE OF THE INVENTION

The invention is an improvement in a process for recovering rIFN-$\beta$ from transformed microorganisms containing the rIFN-$\beta$ in insoluble inclusion or refractile bodies. The rIFN-$\beta$ is separated from the bulk of the cellular components of the microorganisms and solubilized in a reduced form. In the process of the invention, the reduced, solubilized IFN-$\beta$ preparation is oxidized in a chaotropic environment and thereafter renatured in the presence of a stabilizing additive, and then purified to clinically acceptable pyrogen and endotoxin specifications.

The invention comprises oxidizing the denatured, recovered rIFN-$\beta$ from bacteria by placing the rIFN-$\beta$ disposed in a solution of a chaotropic agent (after removing any solids from the solution) into contact with an oxidizing agent, and thereafter renaturing the rIFN-$\beta$ from the solution in the presence of a stabilizing additive. In this way a renatured, oxidized, purified rIFN-$\beta$ having improved water solubility and stability is obtained.

Thus, in one aspect, the invention relates to a process to obtain purified, biologically active, bacterially produced IFN-$\beta$, wherein the process comprises subjecting reduced, solubilized, bacterially produced IFN-$\beta$ in a chaotropic environment to oxidizing conditions, and then removing the chaotropic environment in the presence of an effective amount of solubilizing additive. The oxidized form is better capable of surviving the renaturation conditions and refolding to the proper form, and can be maintained solubilized by the addition of the stabilizing additive.

Other aspects of this invention relate to the renatured, oxidized, purified rIFN-$\beta$ that is prepared by the above-described improved process, and pharmaceutical compositions containing this material.

MODES FOR CARRYING OUT THE INVENTION

A. Definitions

As used herein, the term "rIFN-$\beta$" refers to recombinant IFN-$\beta$ produced by a transformed microorganism and whose amino acid sequence is the same as or similar or substantially homologous to the unglycosylated and-/or glycosylated native IFN-$\beta$.

The rIFN-$\beta$ proteins particularly preferred herein are those biologically active muteins (analogs) of human IFN-$\beta$ in which amino acid residues not essential to biological activity have been deliberately deleted in some instances (as indicated below) or replaced with a conservative amino acid. More specifically, preferred rIFN-$\beta$ proteins include those wherein the cysteine residue at position 17 is replaced with another amino acid, preferably neutral or conservative, to eliminate sites for intermolecular crosslinking or incorrect intramolecular disulfide bond formation. More particularly, preferred rIFN-$\beta$ muteins in the formulations of this invention are those wherein the cysteine residue at amino acid position 17 of the native counterpart is replaced by a serine residue (designated IFN-$\beta_{ser17}$) or alanine residue (designated IFN-$\beta_{ala17}$).

The precise chemical structure of the rIFN-$\beta$ will depend on a number of factors. As ionizable amino and carboxyl groups are present in the molecule, a particular rIFN-$\beta$ may be obtained as an acidic or basic salt, or in neutral form. All such preparations which retain their activity when placed in suitable environmental conditions are included in the definition of "rIFN-$\beta$." Further, the primary amino acid sequence of the protein may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of rIFN-$\beta$ herein so long as the activity of the protein, as defined above, is not destroyed. It is expected, of course, that such modifications may quantitatively or qualitatively affect biological activity, either by enhancing or diminishing the activity of the protein in the various assays.

As used herein the term "transformed" in describing host microorganism cell cultures denotes a microorganism that has been genetically engineered to produce rIFN-$\beta$ that possesses the activity of native IFN-$\beta$. Bacteria are preferred microorganisms for producing rIFN-$\beta$. *E. coli* is particularly preferred.

"Chaotropic environment" refers to an environment in which proteins are denatured or changed from their ordinary conformations. Chaotropic environments may be engendered by the presence of suitable concentrations of chaotropic agents, as described below, or may be the result of heat or pH alterations. The resultant environments are capable of disrupting hydrogen bonding in the protein and altering the thermodynamics of the surroundings in such a way that alternate three-dimensional conformations are preferred in the chaotropic environment to those found in more physiologically compatible environments.

The term "chaotropic agent" refers to a compound or compounds which, in aqueous solution and in a suitable concentration, engender a chaotropic environment and are capable of denaturing rIFN-$\beta$. Guanidine salts (e.g. the hydrochloride) and alkali metal thiocyanates (e.g., sodium thiocyanate) and urea o at concentrations in the range of about 4 to 9 M. preferably 6 to 9 M, are examples of chaotropic environments that will dissolve and denature rIFN-$\beta$.

"Reducing conditions" are those required to place or maintain the IFN-$\beta$ in reduced form with respect to the cysteine residues. These conditions can most simply be provided by use of a suitable reducing agent (especially a thiol-containing reducing agent), or if the IFN-$\beta$ is already reduced (e.g., in the cellular environment), exclusion of air and oxidation catalysts or reagents may suffice.

"Stabilizing" additive refers to a substance or mixture of substances which will keep the referenced protein (rIFN-B) from coming out of solution. Suitable additives include alcohols and polyols, such as sugars, and detergents, as further described below.

B. Cell Growth

The rIFN-$\beta$-producing transformed microorganisms are grown in a suitable growth medium, typically to an optical density (OD) of at least about 10 at 680 nm and preferably between about 20 and 40 at 680 nm. The composition of the growth medium will depend upon the particular microorganism involved. The medium is an aqueous medium containing compounds that fulfill the nutritional requirements of the microorganism. Growth media will typically contain assimilable sources of carbon and nitrogen, energy sources, magnesium, potassium and sodium ions, and optionally amino acids and purine and pyrimidine bases. (See *Review of Medical Biology*, Lange Medical Publications, 14th Ed PP. 80-85 (1980).) In expression vectors involving the trp promoter, the tryptophan concentration in the medium is carefully controlled to become limiting at the time protein expression is desired or an inducer such as IAA is employed. Expression vectors wherein the gene sequence encoding IFN-$\beta$ is under the control of the $P_L$ promoter are maintained in a strain such as *E. coli* MC1000 or DG166 $\lambda$ lysogens and the culture maintained at low temperature until growth is achieved. Then the temperature of the surroundings increased to a suitable temperature for induction, around 40°-43° C. and expression of the gene encoding IFN-$\beta$ is thereby induced. Growth media for *E. coli* are well known in the art.

After the cells are harvested from the culture, they may be concentrated, if necessary, to about 20 to 150 mg/ml, preferably 80 to 100 mg/ml (OD 40 to 300, preferably 160 to 200 at 680 nm) by cross-flow filtration, centrifugation, or other conventional methods. Preferably a compound which is nontoxic to humans, such as 1-octanol, in an amount of about 1% by weight of total components, is added to the fermenter before or during cell concentration to ensure that no viable recombinant organisms remain before cell membrane containment is broken.

C. Cell Disruption

Following concentration of the harvested culture, the cell membranes of the microorganisms are disrupted. Conventional cell disruption techniques such as homogenization, sonication, digestion with lysozyme, or pressure cycling may be used in this step of the process. The end point of the disruption step can be determined by monitoring the optical density, with the absorbance at 260 nm of the suspension typically increasing with cell lysis. In any event, the disruption should break substantially all of the cells so that substantially no intact cells are carried through to subsequent steps.

D. Treatment of Disruptate to Isolate Insoluble rIFN-$\beta$

After the cells have been disrupted, deionized water is preferably added to the disruptate and greater than 99% by weight of the salts are removed by solubilization as they contain water soluble, oppositely charged small molecular weight ions. The removal of these salts to reduce the ionic strength of the disruptate may be accomplished by diafiltration using deionized water to flush out the ions or by centrifuging to pellet the solids followed by resuspension in deionized water. If diafiltration is employed, preferably deionized water is continuously added such that the rate of addition of water equals the filtration rate.

After the salts are essentially removed, optionally a compound such as 1-octanol may be added to the desalted disruptate, if not added earlier, to ensure that no viable recombinant organisms remain before containment is broken. The desalted disruptate is again disrupted as described above for the initial disruption.

After redisruption, density or viscosity is increased and/or a gradient is created during centrifugation in the liquid within the disruptate by adding a material to the disruptate. There are several means to accomplish this purpose, all relying on the sedimentation characteristics of the particles by varying the density and/or viscosity of the liquid phase. One means to accomplish this goal is to add a material which increases the density of the liquid to a $\rho$ of about 1.1 to 1.3 g/ml. preferably 1.13 to 1.17 g/ml.

Materials which may be used to accomplish this density increase include a sugar or mixture of sugars such as, e.g., sucrose, dextrose, fructose maltose, maltotriose, and other mono-. di- or polysaccharides. Most preferably the sugar is sucrose. Alternatively, a two-phase system of materials such as e.g., a glycerol/sucrose mixture may be used wherein the disrupted particles partition to the interface between the heavy and light phases and can be eluted by a liquid/liquid separation.

In addition, the viscosity of the liquid phase may be increased from 5 to 10 cps by any suitable means such as by adding a viscous compound such as. e.g., sucrose or glycerol thereto. Also, a gradient is created if. e.g., the particles are in a 60% aqueous glycerol suspension while the centrifuge bowl contains 80% aqueous glycerol.

The rIFN-$\beta$-containing refractile bodies are then separated from the cellular debris by high-speed centrifugation. By "high-speed centrifugation" is meant spinning the suspension in a centrifuge at about 10 000 to 40,000 times gravity (g). preferably about 10,000-20,000 x g for a suitable time period depending on the volume, generally about 10 minutes to 72 hours. At the end of this step, the bulk of the cellular components of the microorganisms have been separated from the rIFN-$\beta$. In this regard the particle pellet or paste resulting from the centrifugation contains approximately 10-80% by weight IFN-$\beta$ as determined by Lowry assay (Lowry et al. *J Biol Chem* (1951) 193:265-275) and scans of Coomassie-stained SDS gels.

In the alternative, following the procedure described by Moscheva, J. A.. et al, *Methods in Enzymology* (1986) 170:177-183, frozen live *E. coli* cell paste is thawed in a suspension of 4 volumes of buffer containing 0.1 M Tris-HCl. pH 7.9, 50 mM EDTA, 0.1 mM PMSF. and 1 mg/ml lysozyme is added. The suspension is incubated at 4° C. for about an hour while stirring and the suspension is filtered through two layers of cheese cloth and passed through a Manton-Gaulin homogenizer at 7000 psi. The suspension exiting the press is diluted with a volume of buffer containing 10% pEG 6000, 8% potassium phosphate, pH 7.9, to 2 volumes of lysate. The mixture is stirred and decanted into centrifugation holders and centrifuged at 3500 rpm for 1-2 hr in orvall RC-3B centrifuge. The pellet can then be used as the starting material for solubilization.

E. Solubilization of rIFN-β rIFN-β-containing particle pellet or paste is solubilized by providing a chaotropic environment under reducing conditions, which may include a reducing agent. The chaotropic environment may be provided by an aqueous solution of a chaotropic agent or, in the alternative, an aqueous solution wherein other chaotropic conditions are imposed, such as heat or high pH. Preferred chaotropic environments include 2–8 M urea. 3–7 M thiocyanate salts, or about 7 M guanidine hydrochloride. About 7 M guanidine hydrochloride is preferred.

The solubilizing medium also provides reducing conditions to break disulfide bonds and to prevent the solubilized rIFN-β from undergoing oxidation to any significant degree. The protein may already be reduced and exclusion of oxidizing may be adequate. However, it may be convenient to use protein reducing agents, especially thiols, such as DTT and 2-mercaptoethanol. The concentration of reducing agent such as DTT in the medium will usually range between about 5 to 30 mM preferably about 20 mM. The solubilization will typically be carried out at temperatures in the range of 20° C. to 25° C. with mixing. The pH, if necessary, may be adjusted to a range of 8 to 9, most preferably approximately 8.5. The suspension may be heated to 50°±5° C. for 5 to 15 minutes under nitrogen. The reaction mixture is then cooled to approximately 25° C.

The solubilization is considered complete using an arbitrary reaction time, e.g., several hours or when the solution turns translucent. Optionally, any insoluble material may be separated by centrifugation or filtration after completing the solubilization.

F. Removal of Reducing Agent

If a reducing agent has been used, the next step in the process is to remove any reducing agent from the solubilized rIFN-β so that the solubilized rIFN-B may be oxidized. Gel filtration is a preferred way of removing the reducing agent. Gels that are capable of providing the degree of resolution required to separate the reducing agent from the solubilized rIFN-β are commercially available. When DTT is used as the reducing agent, Sephacryl S-200 is a preferred gel; Sephadex G-25 can also be used. The gel filtration will typically be run in buffered solutions (pH 5.5 to 7.0) containing about 0.5 to 7 M of the denaturing agent or otherwise under conditions to maintain the denaturing environment. The gel column will be sized to permit suitable resolution of the components.

Diafiltration may be used as an alternative to gel filtration to remove the reducing agent, maintaining the chaotropic environment.

G. Oxidation of rIFN-β

The rIFN-β is next subjected to a controlled oxidation, preferred controlled oxidation procedures are described in commonly owned U.S. Pat. Nos. 4,172,798 (using an oxidation promoter containing a $Cu^{+2}$ cation such as from $CuCl_2$, $Cu(NO_3)_2$, etc) and 4,530,787 (using o-iodosobenzoic acid). the disclosures of which are incorporated herein by reference. The $Cu^{+2}$ oxidation comprises reacting the aqueous solution of rIFN-β at a pH between about 5.5 and 9, preferably 6 to 8, and most preferably about 7.5, in the presence of air with at least an effective amount of an oxidation promoter containing a $Cu^{+2}$ cation. Controlled oxidation causes the formation of disulfide bridging in the rIFN-β which conforms to the bridging in native IFN-β with no or minimal overoxidation and formation of nonconforming bridging or oligomers. Such oxidation enables the production of high yields of the recombinant IFN-β with the proper disulfide bridging.

The amount of oxidant or oxidation promoter employed is at least an effective amount for oxidation, i.e., an amount which at minimum will be necessary to conduct the oxidation reaction effectively within a convenient period of time. An effective amount is the amount approximately equivalent to the concentration of free sulfhydryl groups in the rIFN-β which are destined to be involved in forming the desired disulfide bonds. Preferably, the amount of $CuCl_2$ will range from about 5 to 275 micromolar. In the case of o-iodosobenzoic acid the mole ratio of oxidant to rIFN-β will preferably be in the range of about 0.05:1 to about 5:1, most preferably about 0.8:1 to about 2:1. The concentration of rIFN-β in the reaction mixture is kept low. i.e., generally less than about 5 mg/ml. preferably about 0.05 to about 2 mg/ml, and more preferably about 0.1 to about 1 mg/ml, to reduce the likelihood of oligomer formation. The pH is maintained between 5.5 and 9, preferably between 7 and 8 in the o-iodosobenzoic acid oxidation.

The temperature used in the oxidation will normally be between about 20° C. and 40° C., conveniently room temperature. For $Cu^{+2}$ oxidation, increasing the reaction temperature increases the rate of reaction. The oxidation reaction may be effectively terminated by such methods as lowering the pH to a level at which the reaction ceases, freezing the solution, or adding chelators such as EDTA to the reaction mixture. Oxidation time will normally be in the range of about 4 hr to about one day.

I. Renaturation of Oxidized rIFN-β

The chaotropic environment is removed from the rIFN-β using a replacement medium which contains a stabilizing additive. If the chaotropic agent is, for example, removed by dialysis against aqueous buffer such as phosphate buffer, aggregation occurs and loss in yield results. However, if dialysis is conducted against a solution containing a stabilizing additive, this is prevented. Thus, in general, renaturation consists of removing the chaotropic environment from the β-interferon under conditions which maintain contact of the β-interferon with a stabilizing additive. Dialysis and diafiltration are suitable methods, and if the denaturing environment is created by elevated temperatures, lowering thereof. The dialysis or diafiltration is done against a medium containing the stabilizing additive; lowering of temperature. similarly, is conducted after addition of stabilizing materials to the medium.

Stabilizing additives are basically of two types, detergents and nondetergents. The detergents are capable of effective behavior at relatively low concentrations of approximately 0.001%–2%; the nondetergent additive concentrations are on the order of at least 5%. Typical detergent additives include, for example, Trycol ® at 0.05–2%; Durfax ® 80 at 0.05–2%; Pluraface ® C17 at 0.05%–2%: and Tween ® 80 at 0.06–2%. Combinations of these detergents can also be used, with the total concentration being in the range of that listed for individual components.

Nondetergent additives, typically alcohols or polyols, including sugars, are useful as stabilizing additives in the present invention. Representative nondetergent additives include glycerol, mannitol, inositol, sucrose and dextrose. Also useful are polymers of diols, such as polyethylene glycol. preferred additives include glycerol, polyethylene glycol of 100–2000 MW. sucrose, and isopropanol. Concentrations required are of the order of at least 5%: a preferred concentration range is 5–50%.

Nondetergent additives can also be used in admixture with detergent additives at compromise concentrations, according to the particular choice of additives selected.

Exemplary stabilizing agents include:

1. A mixture of ethoxylated fatty alcohol ethers and lauryl ether having the formula:

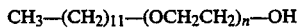

wherein n is an integer between 10 and 14, inclusively.

2. A mixture of modified oxyethylated and/or oxypropylated straight-chain alcohols having the formulas:

wherein p is an integer between 1 and 10, inclusively:
wherein q is zero or an integer between 1 and 10, inclusively; and
wherein r is an integer between 6 and 14, inclusively.

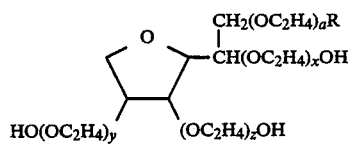

wherein the sum of the integers a, x, y, and z equals 20 and R is a fatty acid having from about 10 to about 20 carbon atoms; more preferably wherein R is a fatty acid having from about 12 to about 18 carbons; and more preferably wherein R is oleic acid, said ester is a polysorbate 80 compound.

4. Polyoxyethylene (12) lauryl alcohol such as Trycol ® LAL-12 (Emery Chemicals, Mauldin, SC) Macole ® LA-12 (Mazer Chemicals, Gournec, Il), and Siponice ® L-12 (Alcolac. Ltd., Quebec, Canada) which are mixtures of ethoxylated fatty alcohol ethers and lauryl ether compounds having the formulas

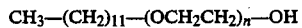

wherein n is a distribution from 1–30 and preferably centering on n~12 and m is a distribution from 9–17 containing a significant proportion of m=11.

5. Pluraface ® C-17 (BASF Wyandotte, Parsippany, N.J.) which is a mixture of modified oxyethylated and/or oxypropylated straight-chain alcohols having the formulas:

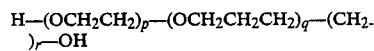

wherein p is an integer between 1 and 5, inclusively: q is zero or an integer between 1 and 5, inclusively: and r is an integer between 10 and 12, inclusively.

6. Durfaxe ® 80 (SCM Durkee Foods, Cleveland, Ohio) or Tween ® 80 (ICI Americas, Inc, Wilmington, Del.) which are polysorbate 80 compounds having the formula:

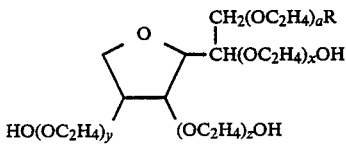

wherein the sum of the integers a, x, y and z equals 20 and R is oleic acid.

Further biodegradable non-ionic polymeric detergents having the above-noted parameters can be found in editions of McCutcheon's Emulsifiers & Detergents published by the McCutcheon Division of MC Publishing Co., 175 Rock Road, Glen Rock, N.J. (U.S.A.). Such non-ionic polymeric detergents can also be employed in the method of this invention.

Thus, in general, the ordinary procedures of removal of the chaotropic environment are employed, such as dialysis or dilution, but the environment is replaced by one containing a stabilizing additive wherein the concentration of the stabilizing additive is maintained within the 0.05–2% for detergents and at least 5% for the non-detergent, range during removal of the chaotropic agent in order to prevent undesired aggregation and loss of yield.

If an rIFN-$\beta$ which does not have the cysteine residue at position 17 replaced with a neutral amino acid (such as rIFN-$\beta$ having the amino acid sequence of native IFN-$\beta$) is being renatured, it has been observed that a significant amount of IFN-$\beta$ isomers having different disulfide bridging than native IFN-$\beta$ are formed. For this reason, it is preferred to carry out this process on rIFN-$\beta$s in which the cysteine residue at 17 is so replaced.

G. Further purification

Following the renaturation the renatured rIFN-$\beta$ may be further purified by conventional methods such as ion exchange chromatography to remove other forms of the protein. The solution of renatured rIFN-$\beta$ is contacted with the exchanger under the appropriate conditions and the rIFN-$\beta$ is eluted with separation from some impurities. Additional purification methods which may be useful are size fractionation using molecular sieve chromatography, affinity chromatography using, for example, antibodies directed to the biologically active form of the protein; adsorption chromatography using non-specific supports and also gel-supported electrophoresis.

H. Purification to Remove Endotoxins

Following oxidation and renaturation, the rIFN-$\beta$ is purified to remove pyrogens and endotoxins to a level that meets clinical specifications (i.e., less than about 0.1 ng endotoxin per mg of rIFN-$\beta$ and substantially free of pyrogens as measured by the U.S.P. rabbit pyrogen test at a dosage of $1.0 \times 10^3$ units/kg). Rp-HpLC and organic extraction are preferred methods for effecting such purification.

1. Formulation

The purified IFN-$\beta$ is formulated in aqueous solution at a concentration in the range of about 0.01 to 2 mg/ml. A water-soluble carrier is added to the desired level. The carrier will typically be added such that it is present in the solution at about 1% to 10% by weight. preferably about 5% by weight. The exact amount of carrier added is not critical. Conventional solid bulking agents that are used in pharmaceutical tablet formulation may be used as the carrier. These materials are water soluble, do not react with the rIFN-$\beta$, and are themselves stable. They are also preferably nonsensitive to water (i.e., nonhygroscopic). Specific examples of carriers that may be added include dextrose, lactose, mannitol, and other reduced sugars such as sorbitol starches and starch hydrolysates derived from wheat, corn, rice, and potato microcrystalline celluloses and albumin such as human serum albumin. Mannitol and dextrose are preferred.

The carrier adds bulk to the formulation such that when unit dosage amounts of the solution are lyophilized in containers, such as sterile vials the freeze-dried residue will be clearly discernible to the naked eye. In this regard the preferred carrier, mannitol, yields an esthetically acceptable (white, crystalline) residue that is not sensitive to water. The nonsensitivity of mannitol to water may enhance the stability of the formulation.

Copending, commonly owned, U.S. patent application Ser. No. 775,751, filed Sept. 13, 1985, entitled "An Improved Formulation for Lipophilic proteins" (Hanisch et al) outlines an improved process for recovering and purifying lipophilic recombinant proteins such as rIFN-$\beta$ from microorganisms to yield a protein preparation which may be formulated into a stable pharmaceutical composition. Such a composition carrying a therapeutically effective amount of the biologically active recombinant lipophilic protein dissolved in a nontoxic, insert, therapeutically compatible aqueous-based carrier medium at a pH of 6.8 to 7.8 also contains a stabilizer for the protein, such as human serum albumin, normal serum albumin and human plasma protein fraction. The formulation aspects of said U.S. Ser. No. 775,751 are herein incorporated by reference as an alternative formulation route for the purified IFN-$\beta$. U.S. Ser. No. 775,751 outlines a low pH formulation process. U.S. Pat. No. 4,462,940 to Hanisch et al. outlines a high pH formulation process, and the formulation aspects thereof are also herein incorporated by reference.

After adding the carrier, the unit dosage amounts (i.e., for rIFN-$\beta$ volumes that will provide 0.01 to 2 mg, preferably 0.2 to 0.3 mg. rIFN-$\beta$ per dose) of the solution are dispensed into containers, the containers are capped with a slotted stopper, and the contents are lyophilized using conventional freeze-drying conditions and apparatus.

The lyophilized, sterile product consists of a mixture of (1) rIFN-$\beta$, (2) carrier (dextrose or mannitol), (3) optionally other excipients such as human serum albumin, Tweene ® 30. and the like. and (4) a small amount of buffer that will provide a physiological pH when the mixture is reconstituted. The product may also contain a minor amount of a preservative to enhance chemical stability. The rIFN-$\beta$ will typically constitute about 0.015% to 3.85% by weight of the mixture, more preferably about 0.4% to 0.6% of the mixture.

The lyophilized mixture may be reconstituted by injecting a conventional parenteral aqueous injection such as distilled water for injection. Ringer's solution injection, Hanks' solution injection, dextrose injection, dextrose and salt injection, physiological saline injection, or the like, into the vial. The injection should be added against the side of the vial to avoid excess foaming. The amount of injection added to the vial will typically be in the range of 1 to 5 ml. preferably 1 to 2 ml.

In an alternative formulation, described in copending U.S. application Ser. No. 749.955, June 26, 1985, and entitled "Solubilization of Recombinant Proteins for Pharmaceutical Compositions Using Homopolymer Conjugation" to M. Knauf et al. the disclosure of which is incorporated herein by reference, the IFN-$\beta$ is reacted with an activated homopolymer selected from polyethylene glycol polypropylene glycol or polybutylene glycol said homopolymer having a molecular weight of from 500 to 20,000 daltons preferably 2000 to 10,000 daltons. The homopolymer is activated by conjugatlon with a coupling agent having terminal groups reactive with both the free amine or thiol groups of the protein and the hydroxyl group of the homopolymer. Examples of such coupling agents include hydroxynitrobenzene sulfonic ester, cyanuric acid chloride, and N-hydroxysuccinimide. The rIFN-$\beta$ is then formulated directly with the water-soluble carrier and buffer as described above, the formulation is lyophilized, and the lyophilized mixture may be reconstituted as described above.

' The reconstituted formulation prepared as described above is suitable for parenteral and oral administration to humans or other mammals in therapeutically effective amounts (i.e., amounts which eliminate or reduce the patient's pathological condition) to provide therapy thereto. rIFN-$\beta$ is appropriate for anti-viral and anticancer therapies and may also be useful in combination with other reagents to enhance their utility.

The formulations of this invention are useful for parenteral administration, for example, intravenous, subcutaneous, intramuscular, intraorbital, ophthalmic, intracapsular, intraspinal, intrasternal, topical, intranasal aerosol, scarification, and also, for oral administration. The preferred routes of administration are by intramuscular. subcutaneous and intravenous injection, and by topical administration, The use of nonionic detergents are especially preferred for topically administered formulations because of their ability to penetrate the skin surface.

The following examples further illustrate the invention. These examples are not intended to limit the invention in any manner. In these examples all temperatures are in degrees Celsius unless otherwise indicated.

EXAMPLE 1

This example illustrates a preferred process for recovering, purifying, renaturing and formulating rIFN-$\beta$.

IFN-$\beta_{ser17}$ was recovered from *E. coli*. The strain of IFN-$\beta_{ser17}$-producing *E. coli* (K12/MM294-1) carrying plasmid pSY2501 used in this example is deposited at the American Type Culture Collection under accession number 39.517. Said analog is disclosed in U.S. Pat. Nos. 4,518,584 and 4,588,585 assigned to Cetus Corporation.

The *E. coli* were grown in a 1000 -liter fermenter at 37° C. The dissolved oxygen is maintained at about 40% by, as necessary. (? ) increasing agitation: (2) adding air; and (3) adding oxygen.

Once the fermenter is filled with water to the operating volume, the following trace elements are added:

| | |
|---|---|
| $ZnSO_4 \cdot 7H_2O$ | 30 μM |
| $MnSO_4 \cdot 4H_2O$ | 30 μM |

-continued

| CuSO4.5H2O | 3 µM |
|---|---|
| Na3 citrate.2H2O | 1.5 mM |
| KH2PO4 | 21 mM |
| (NH4)2SO4 | 72 mM |

The fermenter feed and addition vessels are then sterilized according to standard operating procedures. Then the following sterile additions are made:

| MgSO4 · 7H2O | 3 mM |
|---|---|
| FeSO4 · 7H2O | 72 µM |
| L-tryptophan | 70 mg/L |
| thiamine · HCl | 20 mg/L |
| glucose | 5 g/L |
| tetracycline | 5 mg/L |

The fermenter was cooled and inoculated with frozen of seed E. coli culture at 2 mg/L. A glucose feed is employed to maintain the glucose concentration between 5–10 g/L. At approximately 15 hours after fermentation is begun, the pH is adjusted with KOH to 6.8. Optical density measurements and residual glucose measurements on samples are taken at 14–16 hours and approximately one hour intervals thereafter.

Induction of IFN-$\beta_{ser17}$ production by depletion of L-tryptophan from the culture medium occurs at about $OD_{680}=10$ followed by the addition of casamino acids to a final concentration of 2% at $OD_{680}=15$. Cultures were harvested about 3–5 hours later.

The refractile bodies containing the IFN-$\beta_{ser}17$ were then isolated. The harvested material is concentrated about 5–10 fold by circulating the harvest material under pressure through UF cross-flow filtration cartridges with a 100 K molecular weight cutoff. The cells are disrupted by 3 passes through a disruptor (Manton-Gaulin press) at about 6000–8000 psig.

EDTA was added to 2 mM and the suspension was diafiltered against 5 volumes of deionized water. Octanol was added to 1% (v/v) to kill any residual live bacteria in the diafiltered product. After several hours, the diafiltered disruptate was redisrupted by passing it through a Manton-Gaulin press at 6000–8000 psig.

Sucrose was added to the redisruptate to a concentration of 23% (wt/wt) to create a final density between 1.1 and 1.25 g/ml. The mixture was centrifuged at 10,000 to 20,000 x g at 1–2 lpm and the particle pellet or paste collected. A temperature of at least 20° C. was maintained prior to and during centrifugation.

The particle paste was then solubilized in 7 M guanidine HCl (GuHCl) with 50 mM DTT. The solubilized paste was then centrifuged at 25,000–35,000 x g and the supernatant recovered.

The supernatant was heated to 50°±5° C. for 20 min under nitrogen at a pH of about 8.5. The reaction mixture was then cooled to approximately 25° C., and then the pH of the mixture readjusted to 5.5±0.1 using glacial acetic acid, and the solution filtered through a 0.65 ~m filter.

Chromatographic separation of the lower molecular weight contaminants was achieved using a Sephadexe ® G-25 column. The solubilized and reduced refractile body protein was loaded onto the column and fractions were collected into clean, depyroginated vessels using an elution buffer containing 7 M guanidine HCL at pH 7.5 and 10 mM sodium phosphate buffer pH 5. peak fractions (those falling within 70% of the maximum peak height) were pooled and oxidized as taught below.

The 7 M GuHCl concentration was maintained throughout the solubilization and chromatographic separation procedures.

Oxidation of the rIFN-$\beta$ was initiated by adding CuCl2 in a molar ratio of 3:1 (CuCl2 to rIFN-$\beta$). The oxidation was carried out at about 25° C. The pH was controlled at 7.5±0.2 with 0.5N NaOH during oxidation and 4 mM EDTA was added when the oxidation was completed. Since oxidized rIFN-$\beta$ is more hydrophilic than reduced rIFN-$\beta$, the progress of the oxidation reaction was monitored by Rp-HpLC. Oxidized rIFN-$\beta$ was concentrated using a hollow fiber ultrafiltration unit with a 10K molecular weight cut-off.

EXAMPLE 2

At this point, a stabilizing additive was added to the oxidized IFN-$\beta$ material while guanidine HCl is still present, and the solution was dialyzed to remove the guanidine. The solubilized, oxidized material was divided into aliquots and a different stabilizing agent or a non-ionic detergent was added to each aliquot. A summary of the stabilizing agents and non-ionic detergents used in this example, as well as the concentration used, is provided in Table 1.

TABLE 1

| Reagents to Keep IFN-$\beta$ Soluble as Guanidine HCl in Removed | |
|---|---|
| | Successful (+)/ Unsuccessful (−) |
| 10 mM NaPi, pH5 | − |
| Non-ionic Detergents | |
| Trycol ® LAL-12 (0.3%) | + |
| Trycol ® LAL-12 (0.15%) | + |
| Durfax ® 80 (0.1%) | + |
| Plurafac ® C17 (0.1%) | + |
| Nopalco ® + Triton ® X405 (0.05% + 0.1%) | − |
| Non-Detergents | |
| Ethylene Glycol (20%) | − |
| Propylene Glycol (20%) | − |
| PEG6000 (10%) | − |
| PEG300 (15%) | ± |
| PEG300 (25%) | + |
| Glycerol (25%) | ± |
| 1.2-butanediol (20%) | − |
| 3-penoxy-1,2-propanediol (5%) | − |
| Glucose (50%) | − |
| Sucrose (50%) | ± |
| Isopropanol (20%) | ± |
| Isopropanol (50%) | + |

Each aliquot was dialyzed against 20–50 mM sodium phosphate buffer, pH 5.0 containing the appropriate stabilizer or detergent. The concentration of the stabilizing additive was maintained within the 0.05–2% for detergents and at least 5% for the non-detergents, range throughout the removal of guanidine HCl. Dialysis was run at pH 5.0 because rIFN-$\beta$ is more soluble at low pH than at neutral or higher pH. As the guanidine HCl was dialyzed from the sample, a precipitate formed. The aliquots were centrifuged at 5,000 x g for 15 min and both the supernatant and the pellet, resuspended in 1% SDS were saved. The supernatant and resuspended pellet were analyzed by SDS-pAGE (PHAST system by pharmacia) and silver stain to locate the rIFN-$\beta$.

The results indicate that three non-ionic detergents, Trycole ® LAL-12, Durfaxe ® 80 and Pluraface ® C17 (all at 0.1–0.15% and pH 5) keep greater than 50% of the IFN-$\beta$ in solution. Four non-detergent stabilizers also operate to keep IFN-$\beta$ in solution: 15% PEG300, 25% glycerol, 50% sucrose, and 20% isopropanol. It has also been demonstrated that adjusting concentration and/or pH for any of these stabilizing additives may improve efficacy. For example, Table 2 shows the results of adjusting concentration and pH for glycerol. The results indicate that increasing glycerol concentration to 50% and lowering the pH to 4 results in greater IFN-$\beta$ solubility.

TABLE 2

| Glycerol (25 mM NaPi) | % $A_{280}$ in Supernatant |
|---|---|
| 50%, pH 5 | 50 |
| 50%, pH 4 | 86 |
| 25%, pH 5 | 13 |
| 25%, pH 4 | 31 |

Similar results are seen with $PEG_{300}$.

Combinations of detergents and non-detergent stabilizers were also used in the present solubilization process. For example, 25% glycerol at pH 4 was individually added to 0.01% Tweene ® 80 and 0.01% Trycole ® LAL-12 in the dialysis procedure. Absorbances at 280 nm were measured and SDS-PAGE analysis demonstrated that both of these non-ionic detergents increased the efficacy of glycerol sufficiently to keep most of the IFN-$\beta$ in solution.

EXAMPLE 3

This example provides four purification protocols which can be used singly or in combination with the other protocols for the purification of rIFN-$\beta$.

Ion Exchange Chromatography (IEC)

Solution containing rIFN-$\beta$ is contacted with an appropriate ion exchange material under conditions in which the rIFN-$\beta$ is retained by the exchanger and impurities are removed. rIFN-$\beta$ is then eluted by changing conditions to disrupt the interaction of the rIFN-$\beta$ with the exchanger, for example with a gradient of increasing salt and/or pH. Impurities that are also retained by the exchanger under the initial application conditions may be separated during the elution procedure. Alternatively, the solution containing rIFN-$\beta$ is contacted with the exchanger under conditions in which impurities are retained and the rIFN-$\beta$ elutes.

Hydrophobic Interaction Chromatography (HIC)

Solution containing rIFN-$\beta$ is contacted with an appropriate HIC support under conditions in which the rIFN-$\beta$ is retained by the support and impurities are eluted. rIFN-$\beta$ is then eluted by changing conditions, for example by a gradient of decreasing salt concentration and/or pH change. Alternatively, rIFN-$\beta$ may be contacted with the HIC support under conditions in which impurities are retained and rIFN-$\beta$ elutes.

Size Exclusion Chromatography (SEC)

Solution containing rIFN-$\beta$ is eluted over an appropriate material that separates on the basis of molecular size. The fractions containing rIFN-$\beta$ are recovered and pooled.

Affinity Chromatography

Solution containing rIFN-$\beta$ is contacted with a support material that has been derivitized with a substance that selectively interacts with the rIFN-$\beta$ such as a monoclonal antibody. rIFN-$\beta$ is retained while impurities elute. rIFN-$\beta$ is then eluted by disrupting the specific interaction.

Modifications of the above-described modes for carrying out the invention that are obvious to those skilled in sciences and technologies related to the invention are intended to be within the scope of the following claims.

Deposits

As mentioned above, a culture of E. coli K12/MM294-1 carrying plasmid pSY250I was deposited at the American Type Culture Collection, 12301 Parklawn Drive, Rockville, Md. 20852, U.S. on Nov. 18, 1983 under ATCC No. 39,517.

Said deposit was made pursuant to a contract between the ATCC and the assignee of this patent application, Cetus Corporation. The contract with the ATCC provides for permanent availability of said strain and progeny thereof to the public upon issuance of a U.S. patent related to this application describing and identifying the deposit or upon the publication or laying open to the public of any U.S. or foreign patent application, whichever comes first, and for the availability of the strain and the progeny thereof to one determined by the U.S. Commissioner of patents and Trademarks to be entitled thereto according to 35 USC §122 and the Commissioner's rules pursuant thereto (including 37 CFR §1.14 with particular reference to 886 OG 638). The assignee of the present application has agreed that if the strain on deposit should die or be lost or destroyed When cultivated under suitable conditions it will be promptly replaced upon notification with a viable culture of the same strain.

The deposit under the terms of the Budapest Treaty assure that said culture deposited will be maintained in a viable and uncontaminated condition for a period of at least five years after the most recent request for the furnishing of a sample of the deposited microorganism was received by the ATCC and, in any case, for a period of at least 30 years after the date of the deposit.

Availability of th e deposited strain is not to be construed as a license to practice the invention in contravention of the rights granted under the authority of any government in accordance with its patent laws.

We claim:

1. In a process for recovering purified, biologically active, bacterially produced IFN-$\beta$, wherein the bacterially produced IFN-$\beta$ is separated from the bulk of cellular components of the bacteria, solubilized in a reduced form and thereafter disposed in a chaotropic environment, oxidized, and thereafter purified, the improvement comprising renaturing the oxidized IFN-$\beta$ by removing the chaotropic environment in the presence of a stabilizing additive in an amount effective to maintain the solubility of the oxidized IFN-$\beta$, wherein oxidized IFN-$\beta$ precipitates during removal of the chaotropic environment in the absence of said stabilizing additive, and thereafter purifying the oxidized, soluble IFN-$\beta$.

2. The process of claim 1 wherein the reduced, solubilized IFN-$\beta$ is obtained by dissolving refractile bodies harvested from bacteria, transformed with an expression system for IFN-$\beta$ production and induced for such production, in an aqueous solution of a chaotropic agent in the presence of a reducing agent.

3. The process of claim 1 wherein the chaotropic environment is an aqueous solution of a chaotropic agent.

4. The process of claim 1 wherein the IFN-β is reduced by contacting said IFN-β with a reducing agent.

5. The process of claim 2 wherein the refractile bodies are harvested by lysing the cells and recovering the refractile bodies by centrifuging 6. The process of claim 3 Wherein the chaotropic agent is selected from urea and a guanidinium salt.

7. The process of claim 6 wherein the chaotropic agent is guanidinium chloride.

8. The process of claim 7 wherein the guanidinium chloride is about 7 M.

9. The process of claim 4 wherein the reducing agent is a thiol.

10. The process of claim 9 wherein the thiol is dithiothreitol.

11. The process of claim 1 wherein the oxidizing conditions are provided by cupric ion or o-iodosobenzoic acid.

12. The process of claim 1 wherein the stabilizing additive is a non-ionic detergent.

13. The process of claim 12, wherein said detergent is selected from the group consisting of polyoxyethylene (12) lauryl alcohol; mixtures of modified oxyethylated and oxypropylated straight-chain alcohols; and polysorbate 80 compounds.

14. The process of claim 1 wherein the stabilizing additive is about 5–50% of an alcohol polyol, or sugar.

15. The process of claim 14 wherein the stabilizing additive is selected from glycerol, PEG, sucrose, and isopropanol.

16. The process of claim 15 wherein PEG has a molecular weight range of 100–2,000 daltons.

17. The process of claim 1 wherein the stabilizing additive is an alcohol, polyol, or sugar in combination with a non-ionic detergent.

18. The process of claim 12 wherein a concentration of about 0.001–2% non-ionic detergent is maintained during removal of the chaotropic agent.

19. The process of claim 18 wherein the stabilizing additive is a detergent.

20. The process of claim 17 wherein the stabilizing additive is an alcohol, polyol or sugar and the concentration is greater than or equal to 5%.

21. The process of claim 13 wherein the detergent is Trycol® LAL-12, Durafax®80, Plurafac® C17, and mixtures thereof, and the total concentration of said detergent is in the range of about 0.001 to about 2%.

* * * * *